(12) United States Patent
Magai et al.

(10) Patent No.: US 7,253,632 B2
(45) Date of Patent: Aug. 7, 2007

(54) METHOD FOR QUALIFYING JOINTS AND CONTACTS OF ELECTRIC CIRCUITS

(75) Inventors: István Magai, Biatorbágy (HU); Ferenc Fazekas, Budapest (HU)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/055,142

(22) Filed: Feb. 10, 2005

(65) Prior Publication Data

US 2005/0206391 A1    Sep. 22, 2005

(30) Foreign Application Priority Data

Mar. 16, 2004    (HU) .................................... 0400594

(51) Int. Cl.
*G01N 25/00* (2006.01)
*B23K 11/24* (2006.01)

(52) U.S. Cl. ........................ 324/451; 219/109; 219/110

(58) Field of Classification Search ................ 324/451; 219/109, 110
See application file for complete search history.

(56) References Cited

U.S. PATENT DOCUMENTS

| | | | |
|---|---|---|---|
| 3,213,667 A | * | 10/1965 | Gettys ............................ 374/5 |
| 5,399,827 A | | 3/1995 | Fortmann |
| 5,721,415 A | | 2/1998 | Fortmann et al. |

FOREIGN PATENT DOCUMENTS

| | | | |
|---|---|---|---|
| SU | 688873 A | * | 9/1979 |
| SU | 1583761 A | * | 8/1990 |

OTHER PUBLICATIONS

Altet, J., et al., "Analysis of the feasibility of dynamic thermal testing in digital circuits", Nov. 17, 1997, Test Symposium, 1997, (ATS '97, Proceedings, Sixth Asian Akita, Japan Nov. 17-19, 1997, Los Alamitos, CA USA, *IEEE Comput. Soc., US*, pp. 149-154.

(Continued)

*Primary Examiner*—Andrew H. Hirshfeld
*Assistant Examiner*—Amy He
(74) *Attorney, Agent, or Firm*—Fay Sharpe LLP

(57) ABSTRACT

In a method for qualifying an electric circuit having at least one contact, a reference function of thermoelectric voltage versus time of a faultless electric circuit is provided. The circuit is heated by at least one measuring electric impulse. Thermoelectric-voltage-versus-time data of the electric circuit is acquired. The circuit is qualified based on the differences between the acquired data and the reference function. Additionally, in a method for localizing a weak or bad contact of an electric circuit, the circuit is heated by at least one measuring electric impulse, and thermoelectric-voltage-versus-time data of the circuit is acquired. The acquired data is then compared to reference functions of thermoelectric voltage versus time data of known circuits with weak or bad contacts. The weak or bad contact of the circuit is localized in accordance with the similarities between the acquired data and the reference functions.

19 Claims, 9 Drawing Sheets

OTHER PUBLICATIONS

Altet, J., et al. "Thermal coupling in integrated circuits: application of thermal testing", *IEEE Journal of Solid State Circuits*, vol. 36, No. 1, Jan. 2001, pp. 81-91.

Altet, J., et al., "Differential thermal testing: an approach to its Feasibility", *Journal of Electronic Testing*, Kluwer Academic Publishers, Dordrecht, NL, vol. 14, No. 1/2, Feb. 1998, pp. 57-66.

Altet, Jr., et al., "Differential sensing strategy for dynamic thermal testing of ICs", Apr. 17, 1997, *VLSI Test Symposium*, 1997, 15th IEEE Monteray, Ca, USA, Apr. 27-May 1, 1997, Los Alamitos, Ca, USA, pp. 434-439.

\* cited by examiner

METHOD FOR QUALIFYING JOINTS AND CONTACTS OF ELECTRIC CIRCUITS

BACKGROUND OF THE INVENTION

This invention relates to a method for qualifying joints and contacts of an electric circuit during its production process and at the end of the production process. The invention further relates to a method for localizing a weak or bad contacting joint or contact in the electric circuit.

Methods of spot welding are known in which measuring the thermoelectric voltage between the electrode and the work-piece is the basis of spot weld qualification.

U.S. Pat. No. 5,399,827 discloses a method and apparatus for determining the temperature of a spot-welded joint and a method for assessing the quality of a spot-welded joint. After completion of the welding operation, the welding current is disconnected and the welding electrode with the work-piece, which are composed of different metals, act as a thermocouple. A temperature curve versus time is determined through the measured thermoelectric voltage. Quality of the spot weld is assessed from the course of the temperature versus time.

U.S. Pat. No. 5,721,415 describes a method and apparatus for ascertaining an evaluation time interval for assessing the quality of a spot weld based on a variation in temperature in the evaluation time interval after the spot welding. The temperature course of a good quality spot weld is approximately linear in some regions and in a middle range has a slight upward bulge that can be ascribed to a delay in the temperature drop caused by a heat of solidification at the spot weld.

Both methods described in the patents above use the heat created by the joining operation, that is the spot welding, which induces thermoelectric voltage. This voltage is generated between the work-piece and the welding electrode.

There is a particular need for a method to qualify several joints and contacts of an electric circuit after their manufacturing process, and to detect also the fault of joints, the manufacture of which does not create significant heat, such as crimping and bolting as well as to detect the fault of switches or connectors. The qualification has to be fast and reliable. Furthermore, there is a need for a method to localize the weak or bad contacting joint or contact in a defective electric circuit.

SUMMARY OF THE INVENTION

In an exemplary embodiment of the invention, a method is provided for qualifying an electric circuit having at least one electric joint or contact. A reference function of thermoelectric voltage versus time of a faultless electric circuit is provided. Then, the electric circuit to be qualified is heated by at least one measuring electric impulse. The next step is acquiring the thermoelectric-voltage-versus-time data of the electric circuit. Subsequent steps are: comparing the acquired thermoelectric-voltage-versus-time data to the reference function, and qualifying the electric circuit based on the differences between the acquired data and the reference function.

In an exemplary embodiment of another aspect of the invention, a method for localizing a weak or bad contacting joint or contact of an electric circuit is provided. Reference functions of thermoelectric voltage versus time of different possible locations of the weak or bad contacting joint or contact of the electric circuit are provided. Thereafter, the electric circuit is heated by at least one measuring electric impulse, and subsequently the thermoelectric-voltage-versus-time data of the electric circuit are acquired. Then, the acquired thermoelectric-voltage-versus-time data are compared to the reference functions. The weak or bad contacting joint or contact of the electric circuit is localized in accordance with the similarities between the acquired data and reference functions.

Use of these methods has several advantages over the prior art. Qualification of an electric circuit with several joints and contacts can also be done after the production process. Mechanical joints the production of which is performed without remarkable heat generation, such as crimping, pressing, bolting; and contacts such as connectors or switches can also be qualified. Latent electric contact defect in an electric circuit or in a machine can also be detected and it can be localized.

BRIEF DESCRIPTION OF DRAWINGS

The invention will now be described with reference to enclosed drawings where.

DETAILED DESCRIPTION OF THE INVENTION

Figure 1:
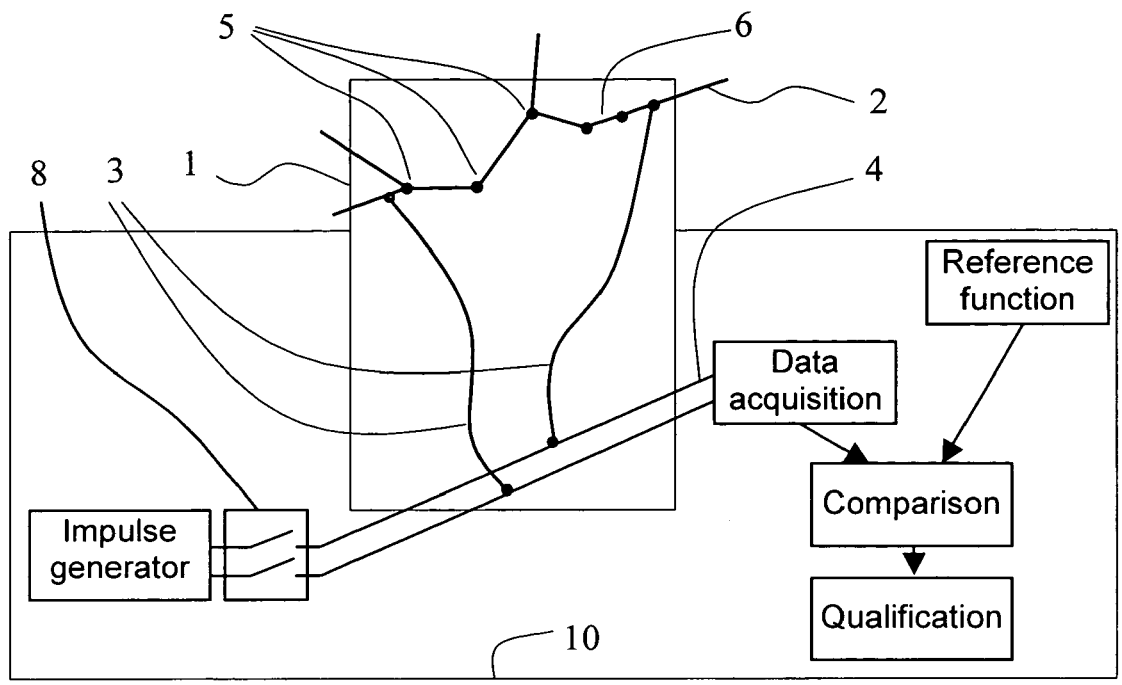
FIG. 1 shows the connection of a measuring apparatus and an electric circuit with joints to be qualified.

Referring now to FIG. 1, a connection of a measuring apparatus 10 and electric circuit 2 to be qualified is shown. The electric circuit 2 consists of joints 5 and contacts 6 and it is connected to connection rails 4 of the measuring apparatus by measuring wires 3. The electric circuit 2 and the measuring wires 3 together form a test circuit 1. Under joints, electric joints made by welding, soldering or mechanical forming such as crimping or pressing are to be understood, while detachable electric joints such as connectors or switches are called contacts. The measuring apparatus 10 includes an impulse generator for generating electric measuring impulse, a connecting means—in this embodiment the measuring wires 3—for connecting the electric circuit 2 to the measuring apparatus, a data acquisition board for acquiring thermoelectric voltage vs. time data, a reference function unit for providing the reference function of a faultless electric circuit, a comparison unit for comparing the acquired thermoelectric voltage vs. time data of the electric circuit 2 to the reference function provided, a qualification unit for qualifying the electric circuit 2 based on the differences between the acquired data and the reference function. Since the contacts of the connecting means are parts of the test circuit 1, the fault of the contacting means, that is the fault of the measuring wires 3 in this embodiment, results in bad qualification also for the electric circuit 2. In order to avoid electric interference during the data acquisition, the test circuit 1 can be disconnected from the impulse generator by a switch 8.

The electric circuit 2 to be qualified is made of different metal parts. The different metal parts joined in the electric circuit create thermocouples. In the present invention, two metal parts are considered different in the event that they induce a thermoelectric voltage that can be measured reproducible, i.e. thermoelectric voltages of substantially the same magnitude and shape in time are repeatedly obtained. When heating the test circuit 1 by a short measuring current impulse, a region of a weak or bad contacting joint or contact is heating up and the thermocouple at the weak or bad contacting joint or contact is inducing thermoelectric voltage. In this context, the region of the weak or bad contacting joint or contact is the small amount of materials situating in the environment of the increased contact resistance.

Subsequently to the heating, the weak or bad contacting joint or contact is cooling down. The thermocouple voltage transient, i.e. the thermoelectric voltage versus time is measured, and the measured data are stored. Depending on the location and the type of weak or bad contacting joint or contact, the thermoelectric-voltage-versus-time data are different. The reference thermoelectric-voltage-versus-time data are recorded from a faultless electric circuit or the reference function is provided by modeling the behavior of the faultless electric circuit during its heating by the measuring electric impulse and its subsequent cooling. As a result of modeling the reference function, a data set or a mathematical expression or at least one numerical value is obtained. The acquired thermoelectric-voltage-versus-time data are compared to the reference function and the electric circuit is qualified as a defective circuit if a predetermined difference exists between the reference function and the measured thermoelectric voltage.

The number of joints and contacts in an electric circuit determines the number of thermocouples in the circuit. The more different metal materials joined or contacted in the electric circuit, the more thermocouples are created. When applying one or more short measuring electric impulses to the electric circuit, the region of the weak or bad contacting joint or contact excited by the short current impulse is heating up and the thermocouple at the weak or bad contacting joint or contact is inducing thermoelectric voltage. The shape of the thermoelectric voltage vs. time diagram is different depending on the location of weak or bad contacting joint or contact. Reference data sets of thermoelectric voltage versus time are assigned to the different possible locations of the weak or bad contacting joint or contact. The shape of the acquired thermoelectric-voltage-versus-time data of the defective electric circuit are compared to the shape of the reference data sets assigned to the different locations of the weak or bad contacting joint or contact. The location of the weak or bad contacting joint or contact is determined in accordance with the similarity of the shape of acquired thermoelectric-voltage-versus-time data to the shape of one of the reference data sets.

Figure 2:
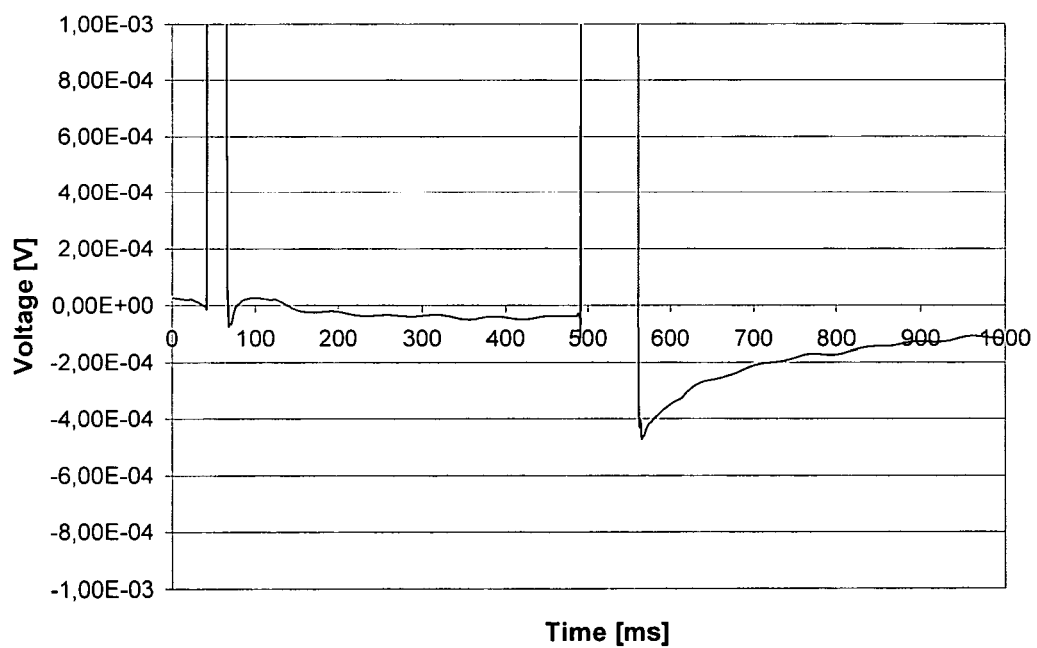
FIG. 2 shows the thermoelectric voltage vs. time diagram of an electric circuit with bad contact between a brass wire and a zinced shoe.

FIG. 2 shows the thermoelectric voltage vs. time diagram of an electric circuit with bad contact between a brass wire and a zinced shoe. Two measuring impulses can be seen in the diagram. After the falling edge of the first shorter measuring impulse, the thermoelectric voltage shows some alteration and takes nearly the same value as the initial voltage value. Having heated the electric circuit by a second measuring impulse, the region of bad contact point between the brass wire and the zinced shoe is heating up and then cooling down. After the falling edge of the second measuring impulse, the thermoelectric voltage shows a negative peak and a cooling curve of the bad contacting region of the brass wire and the zinced shoe.

The invention will now be explained by the example of a filament lamp circuit. In addition to the requirements of usual industrial and domestic applications of filament lamps, automotive industry has special requirements concerning the quality of installed filament lamps. A defective lamp in the process of mass production of automobiles leads to extra cost, while a bad contacting, flashing or shortened lifetime lamp constitutes safety risk in the operation of an automobile.

Efforts have been made to improve the quality of filament lamps. Several check points are evolved in the manufacturing process, and inspection of the faultless operation of lamps is continuously performed at the end of production process.

In spite of the efforts made, to accomplish detection of the bad contacting or flashing lamp is still problematic. The methods known at present use cold or heated electrical resistance as a critical parameter to qualify the filament lamp electric circuit.

Figure 3:
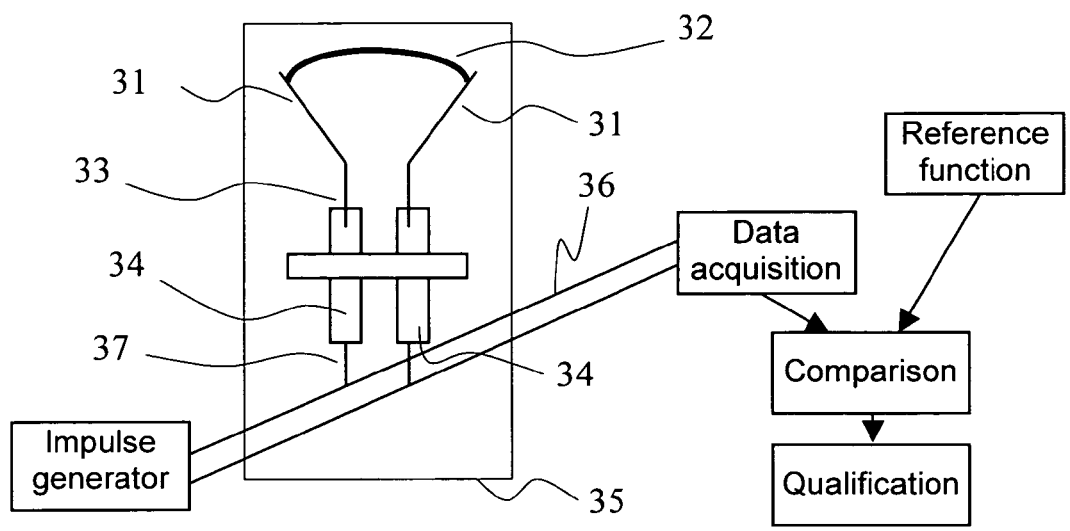
FIG. 3 shows the connection of a filament lamp circuit and the measuring apparatus in a production process.

Referring now to FIG. 3, a connection of a filament lamp circuit and a measuring apparatus is shown in the filament lamp production process. This figure is similar to FIG. 1 with the difference that a filament lamp circuit replaces the electric circuit 2. After creation of joints between electrodes 31 and a filament 32, the qualification of the joints in the filament lamp circuit is to be performed. The electrodes 31 joining to lead-in wires 33 are fixed in holders 34. The lead-in wires 33 connect to an impulse generator and a data acquisition board through connecting rails 36 and measuring wires 37. In this case, the electric circuit to be tested consists of the filament 32, the electrodes 31, the lead-in wires 33, the holders 34, the measuring wires 37 and the contacting joints between them. Similar measuring circuit can be built up at the stage of welding the electrodes 31 and the lead-in wires 33 or at any stage of the critical points of the filament lamp production process.

Figure 4:
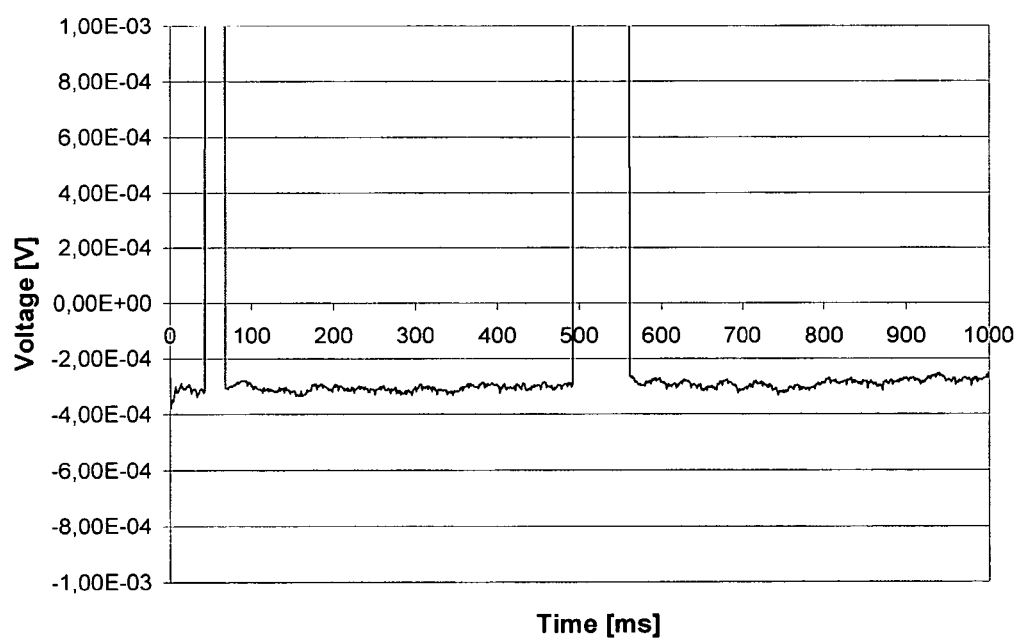
FIG. 4 shows the thermoelectric voltage vs. time diagram of a faultless filament lamp circuit.
Figure 5:
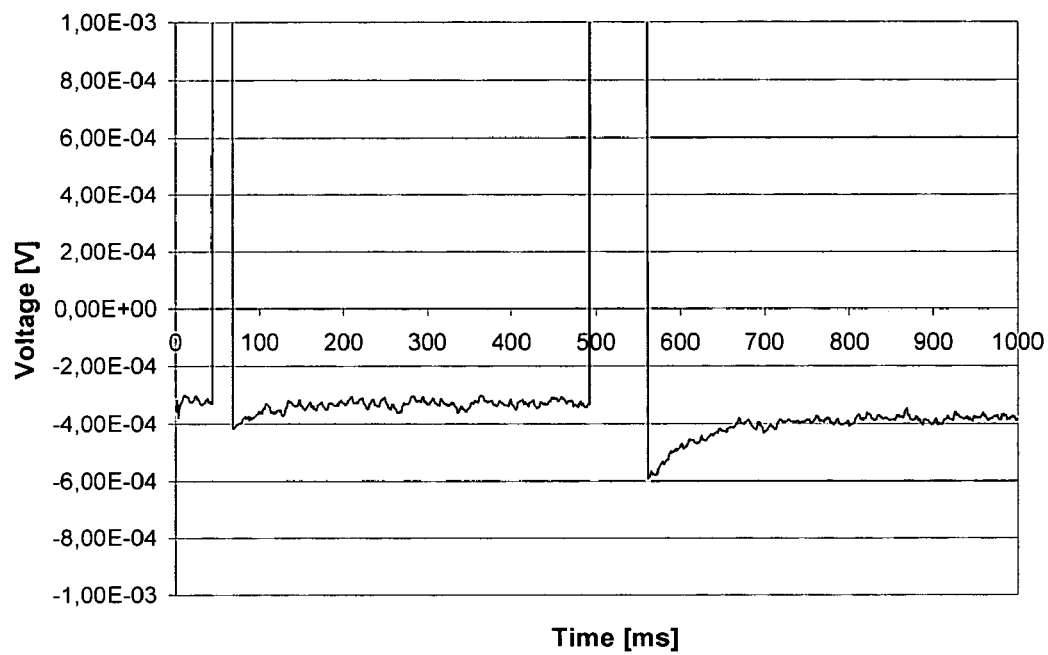
FIG. 5 shows the thermoelectric voltage vs. time diagram of a defective filament lamp circuit.

Referring now to FIGS. 4 and 5, the thermoelectric voltage vs. time diagrams of good quality (non-flashing) and flashing filament lamp circuits are shown.

In FIG. 4, the graph of the thermoelectric-voltage-versus-time data shows that there is no increased contact resistance in the sequence of the joints; there is no heating up by the current of measuring electric impulse. Since no thermoelectric voltage originates from any of the thermocouples created by the joints, the graph is essentially constant, only electromagnetic disturbances superposed to the constant line can be seen.

In FIG. 5, the thermoelectric voltage versus time of a flashing filament lamp circuit is shown. The current of the measuring impulses heated up the filament lamp electric circuit instantly. After the end of measuring electric impulses, natural cooling down of the region of bad contacting joint occurred. The thermoelectric voltage created by the thermocouples at a bad-contacting joint was measured and plotted.

The method for qualifying joints and contacts of an electric circuit can be used in an early stage, at critical points or at the end of production process. At the early stage of filament lamp production process, the filament lamp circuit consists of two metal parts joined together and two holders fixing the metal parts and connecting them to the joining apparatus. Though, at the end of the production process the filament lamp electric circuit consists of the filament, the additional parts which are connecting the filament to the external connectors and the collecting brush of the final test machine of the lamp products. The measuring apparatus is connected to the collecting brush of the final test machine. The term "test circuit" is implicating here the electric circuit as a whole, including the connectors or collectors for connecting the filament lamp to the measuring apparatus.

Figure 6:
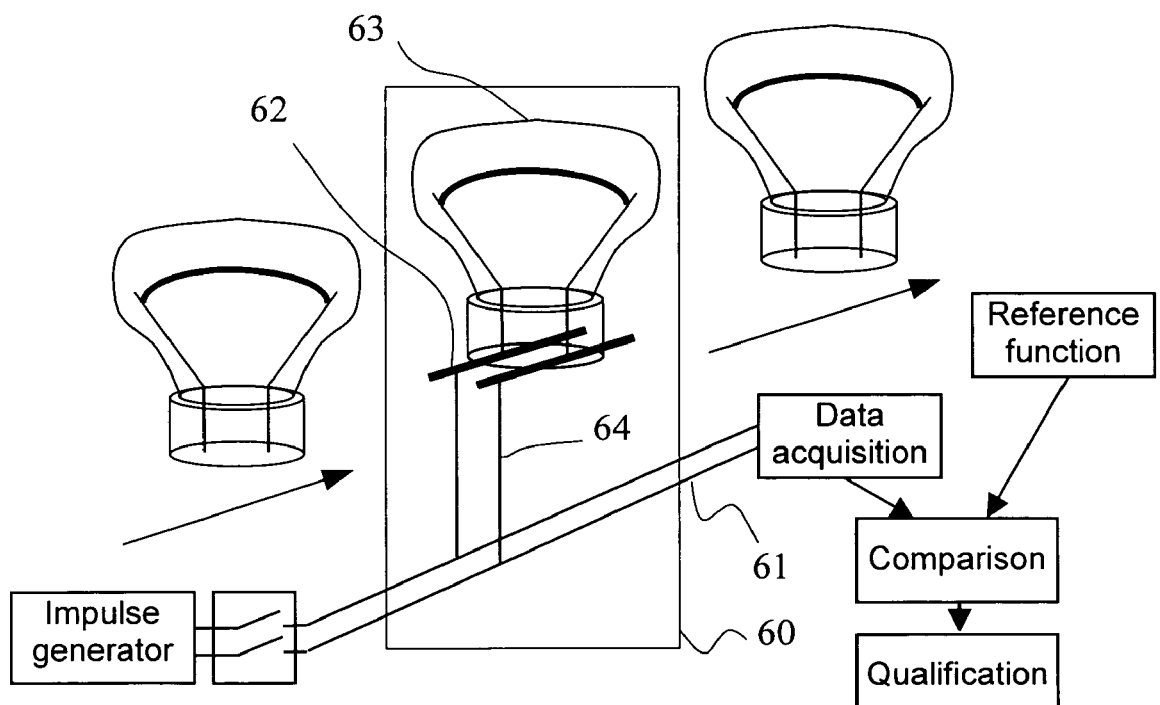
FIG. 6 shows the connection of the measuring apparatus and filament lamps during the final test in the production process.

Referring now to FIG. 6, an arrangement of the measuring apparatus and the filament lamps during the final test in the production process is shown.

FIG. 6 is similar to FIG. 3; however a slight difference is between them, and this difference originates from the qualification of filament lamp circuits during traditional final test of the lamps. At the end of the production process, the filament lamps are moving through the final test process. An investigated lamp 63 from the production line is connected to carbon brushes 62 of the conventional final test machine. Moreover the traditional contact testing, the assessment of joints and contacts of the filament lamp circuit has been performed. The carbon brushes 62 of the test machine are connected to an impulse generator and a data acquisition board by measuring wires 64 and rails 61. In this case, the circuit 60 to be tested consists of the filament lamp 63, the carbon brushes 62, the measuring wires 64 and the rails 61 and the contacting joints between them. The filament lamp circuit appears to be defective, if the filament lamp is defective or the connection between the lamp and measuring apparatus is defective.

Figure 7:
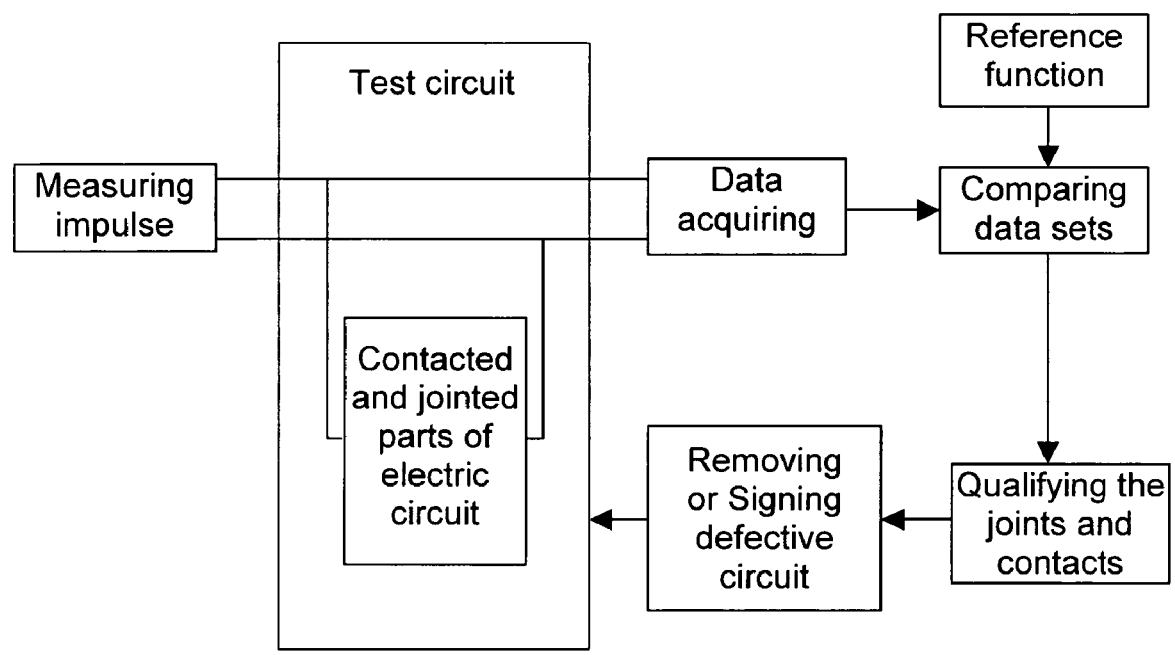
FIG. 7 is the block diagram of a method for qualifying joints and contacts of an electric circuit.

Referring now to FIG. 7, a block diagram of a method for qualifying joints and contacts of a filament lamp electric circuit is shown.

Starting now from the left block of the block diagram, one or more electric measuring impulses are led to contacted and jointed parts of the electric circuit. The amplitude of the measuring impulse is in the range of 1-14 V and its length is between 5-30 ms. The region of a weak or bad contacting joint or contact (if any) is heating up. Since the measurement is to be performed in the environment of a production process, it is preferable if the test circuit is disconnected from the impulse generator after the falling edge of the electric impulses in order to avoid electric interference.

A data acquisition board acquires the thermoelectric-voltage-versus-time data. The data acquisition board is preferably integrated in an industrial computer. Sampling frequency is higher than 1 kHz, voltage range of the data acquisition is between 0.5-5 mV.

The reference data set or reference function belonging to a good quality electric circuit is digitally stored in the measuring apparatus. The reference data set or reference function is compared to the acquired data by digital or analogue electronic equipment. It is preferable if this digital or analogue equipment is integrated in an industrial computer. The comparison of the acquired thermoelectric voltage vs. time data to the reference thermoelectric-voltage-versus-time data set or the reference function previously recorded is based on the examination of differences in the two data sets or alternatively the comparison is based on the differences in shape of graphs plotted on the acquired thermoelectric voltage vs. time data and the reference function.

According to the result of comparison, the electric circuit is qualified as a good quality or a defective circuit. The defective electric circuit is signed or removed from the production process.

Figure 8:
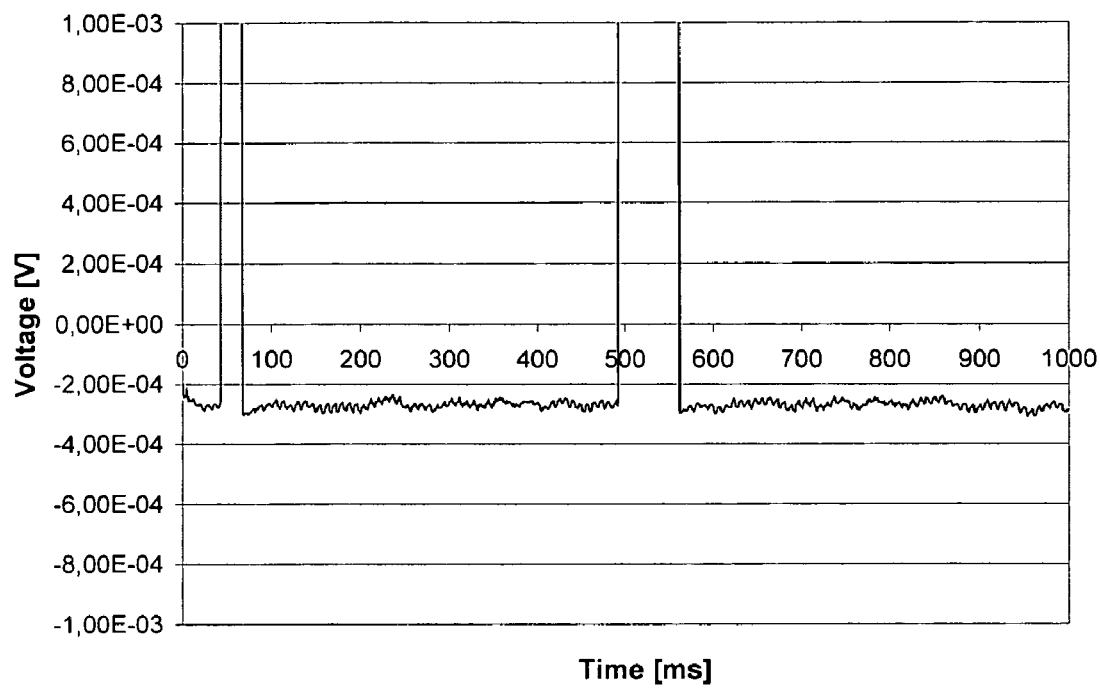
FIG. 8 shows the thermoelectric voltage vs. time diagram of a faultless electric circuit of an automotive reflector with a H7 filament lamp.
Figure 9:
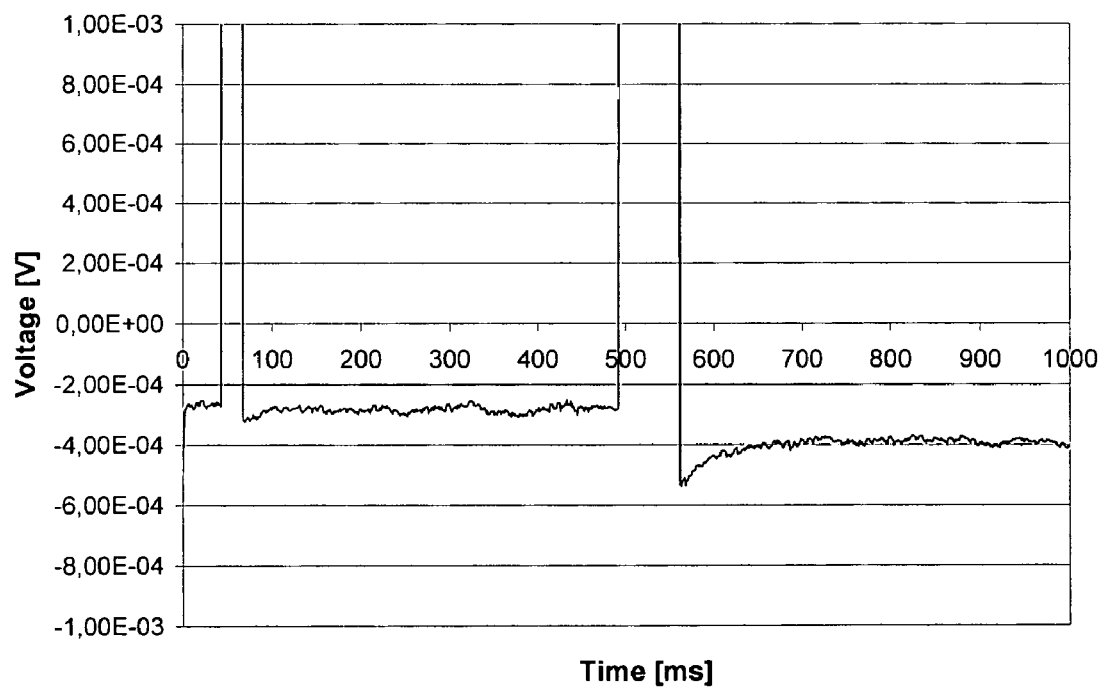
FIG. 9 shows the thermoelectric voltage vs. time diagram of an electric circuit of an automotive reflector with a defective H7 filament lamp.

Referring now to FIG. 8 and FIG. 9, there is shown the thermoelectric voltage vs. time diagram of a faultless electric circuit and that of a defective electric circuit, both circuits belonging to an automotive reflector with H7 filament lamp. In FIG. 8, the diagram of the faultless electric circuit provides only electric disturbance superposed on the base voltage subsequently to each measuring impulse. In FIG. 9, there is no remarkable effect of the first heating impulse, but natural cooling of a bad contacting point can be recognized by the time variation of the thermoelectric voltage appearing subsequently to the falling edge of the longer second impulse.

Figure 10:
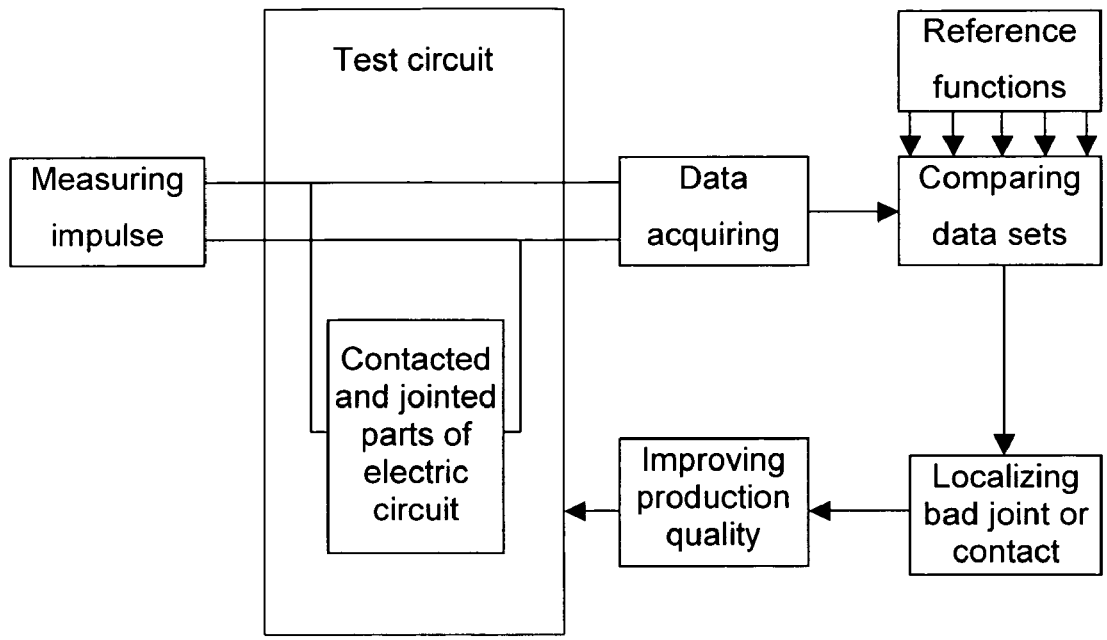
FIG. 10 is the block diagram of a method for localizing a weak or bad contacting joint or contact of an electric circuit.

Referring now to FIG. 10, a block diagram of the method for localizing a weak or bad contacting joint or contact of an electric circuit is shown. The block diagram in this figure is similar to the block diagram of FIG. 7. Differences also exist, they are as follows: reference functions are assigned to the different possible locations of a weak or bad contacting joint or contact of the electric circuit, and they are compared to the acquired data set. Measuring defective electric circuits with different locations of weak or bad contacting joints or contacts provides these reference functions. The location of a defective contact is determined in accordance with the similarity of the shape of acquired thermoelectric-voltage-versus-time data to the shape of one of the reference functions assigned to the different faulty locations. With other words, localization of the weak or bad contacting joint or contact of the electric circuit is based on the similar shape of the voltage graphs of the acquired thermoelectric voltage vs. time data and the reference functions. The information concerning the location of the weak or bad contacting joint or contact can be used to improve the production quality and reliability.

Figure 11:
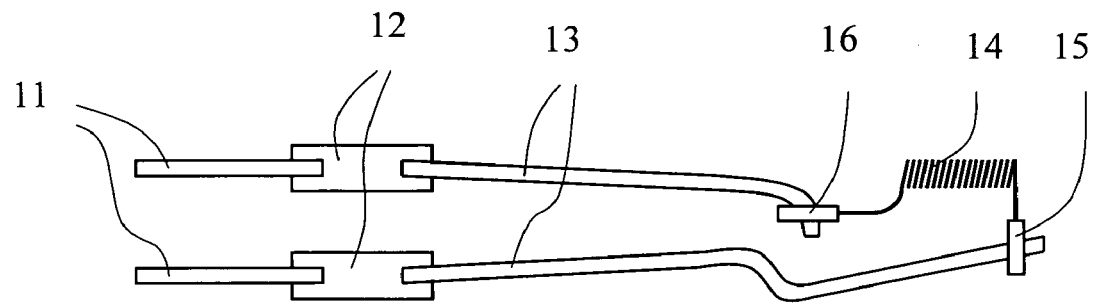
FIG. 11 shows the structure of the electric circuit of a H7 filament lamp.

FIG. 11 shows the structure of the electric circuit of a H7 filament lamp. The lead-in wires 11 are connected to foils 12. The role of the foils 12 is leading the current through the glass of the lamp bulb. The foils 12 are connected to molybdenum electrodes 13 and the molybdenum electrodes 13 are welded to molybdenum pipes 15, 16. The two ends of a tungsten spiral filament 14 are fixed into the molybdenum pipes 15, 16 by pressing the wall of these pipes.

Figure 12:
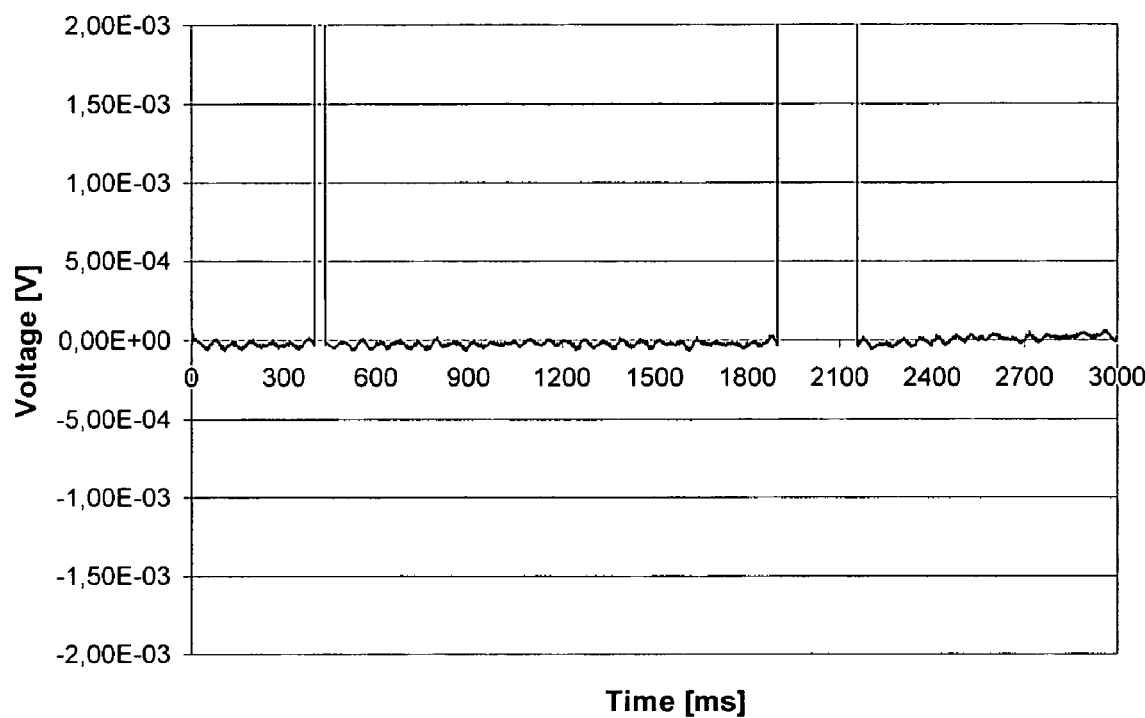
FIG. 12 shows the thermoelectric voltage vs. time diagram of a faultless H7 filament lamp.

FIG. 12 shows the thermoelectric voltage vs. time diagram of a faultless H7 filament lamp. As it can be seen in the diagram, neither the shorter nor the longer measuring impulses produce any heating in the filament electric circuit. If the order of the parts is not symmetric in another lamp construction—for example, there is an additional part between the filament and one of the molybdenum electrodes—the reference function of the faultless filament circuit is different from a constant voltage vs. time curve.

FIG. 13-17 show the thermoelectric voltage vs. time diagrams of H7 filament lamps with different defective joints.

Figure 13:
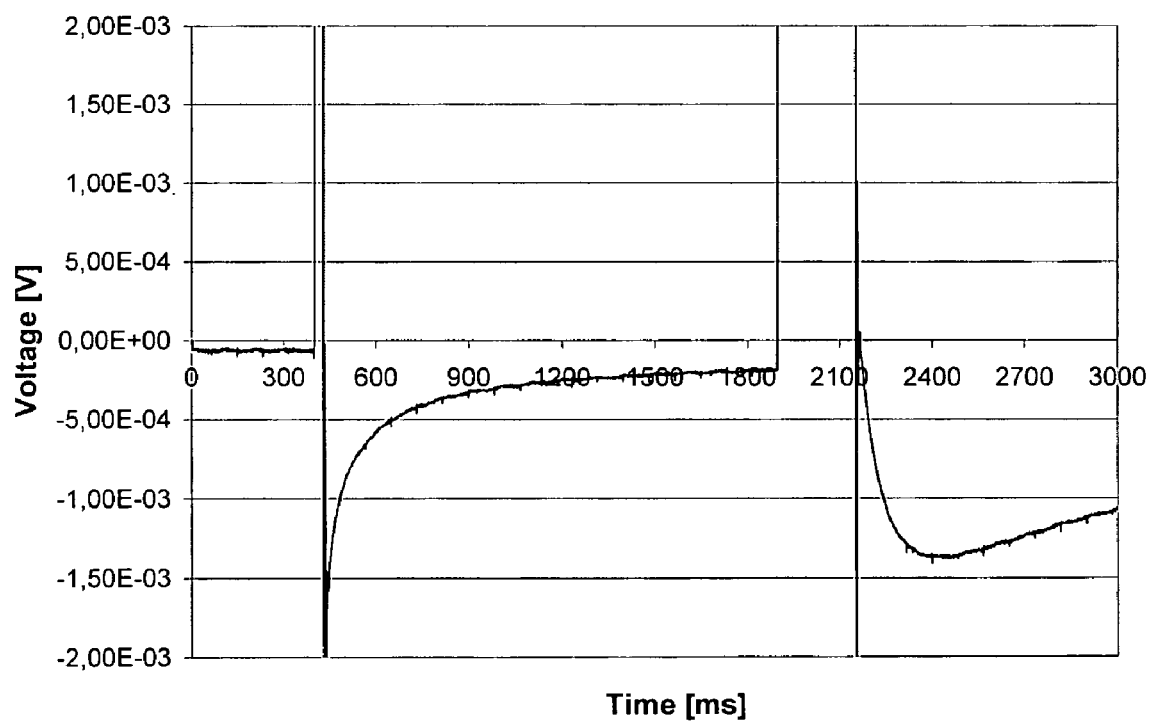
FIG. 13-17 show thermoelectric voltage vs. time diagrams of H7 filament lamps with different defective joints.

In FIG. 13, the time variation of the thermoelectric voltage subsequently to the falling edge of the first and second impulse shows defective electric contact between the molybdenum pipe 15, 16 and the end of the tungsten filament 14.

Figure 14:
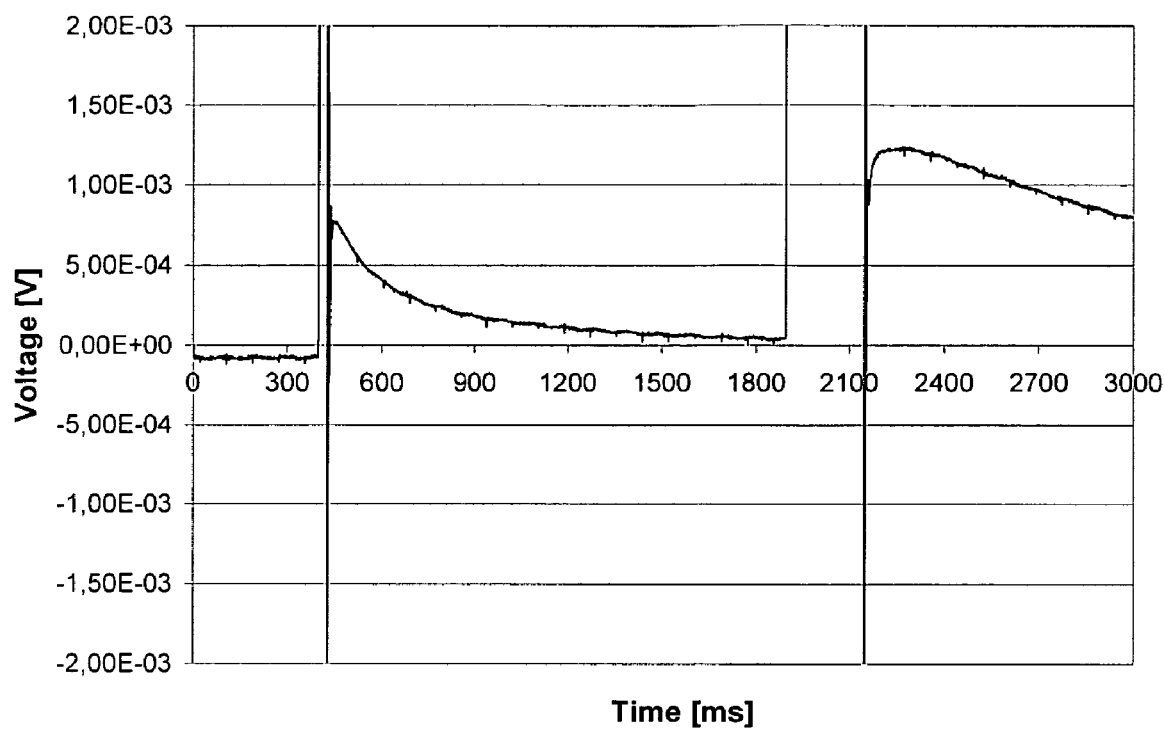

In FIG. 14, the time variation of the thermoelectric voltage subsequently to the falling edges of the impulses shows that the welding joint between the molybdenum pipe 15 and the molybdenum electrode 13 is weak or bad.

Figure 15:
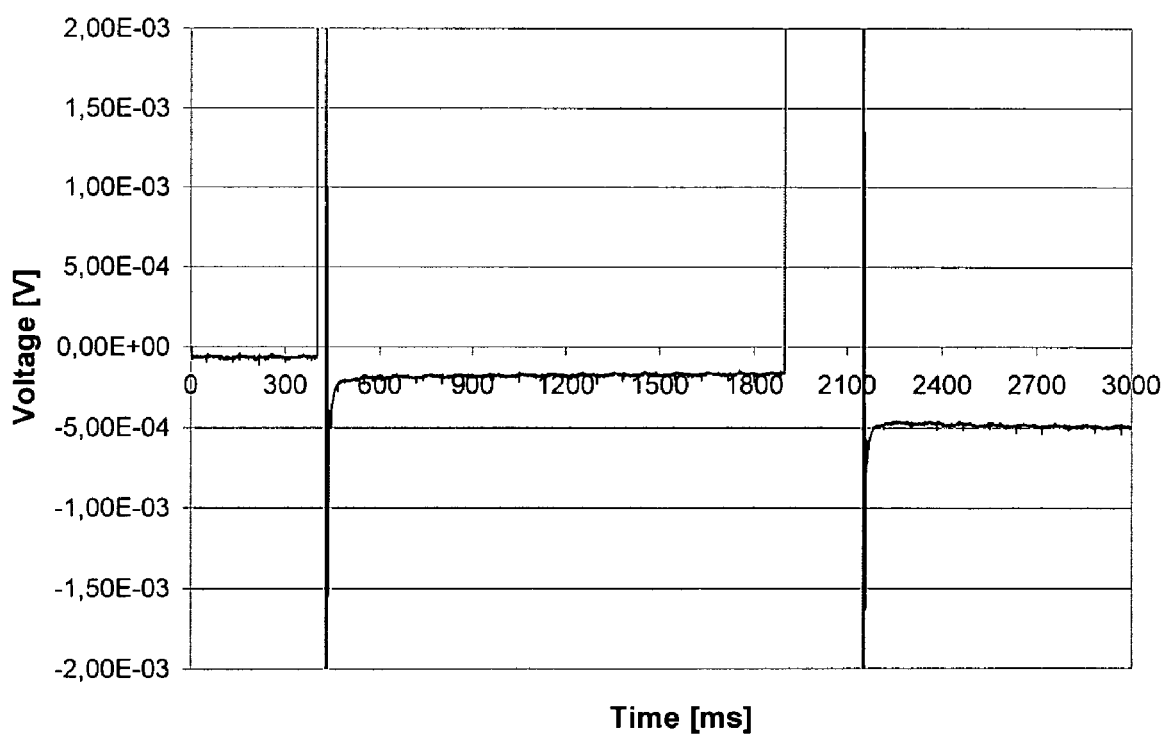

In FIG. 15, the thermoelectric voltages have different magnitudes subsequently to the falling edge of the first and second impulse, respectively. The different magnitudes show a defective contact in the welding joint between the molybdenum pipe 16 and the molybdenum electrode 13.

Figure 16:
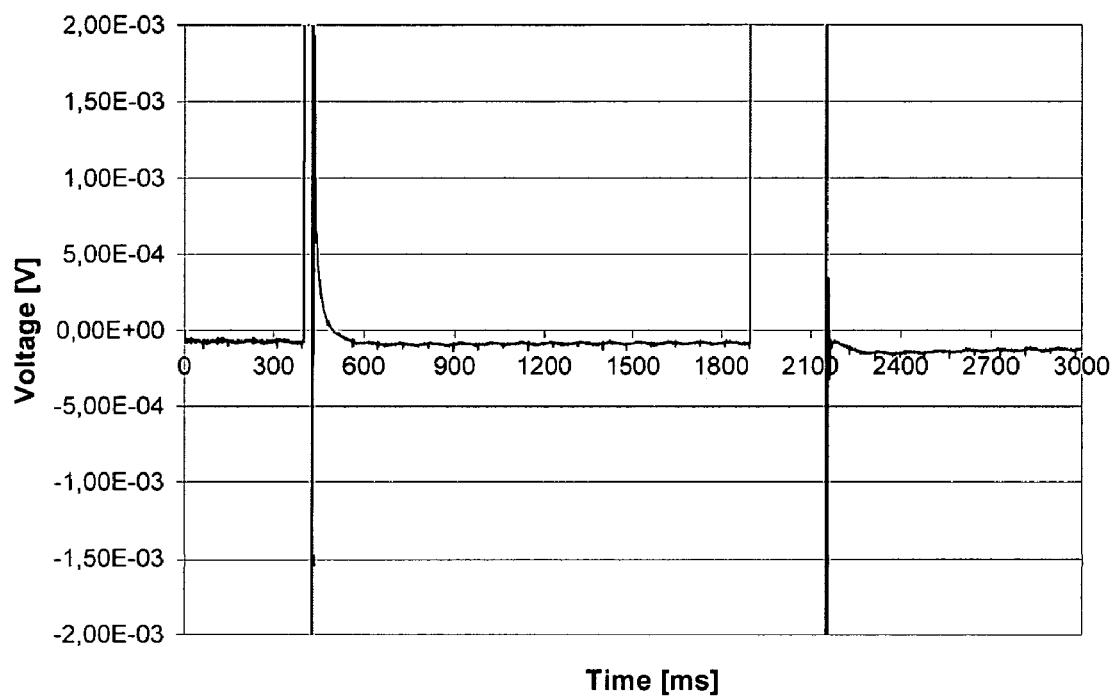
Figure 17:
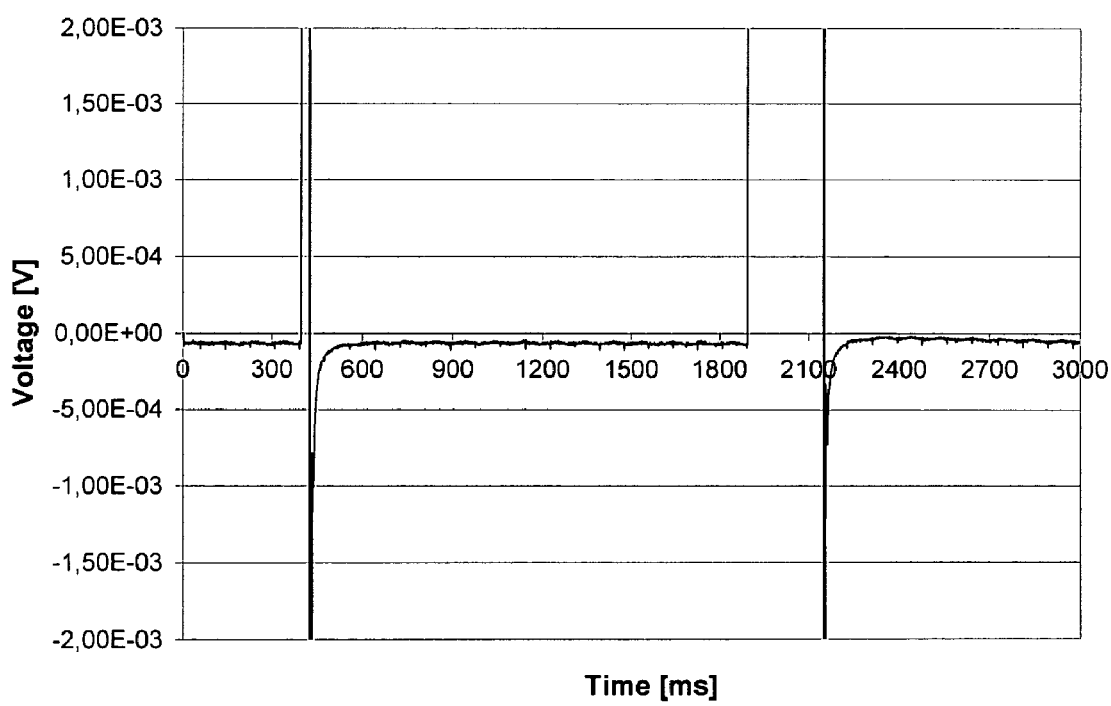

FIGS. 16 and 17 show the time variation of the thermoelectric voltage brought about by identical defects in the molybdenum foil 12. The difference between the two diagrams is that the lamp is connected to the test circuit with different polarities. Characteristic thermoelectric alterations follow the falling edge of the first shorter measuring impulses, while the second longer impulse did not result in a remarkable effect on the diagram of FIG. 16. The use of shorter and longer measuring impulses allows latent defective lamps to be uncovered and the weak or bad contacting joint in a lamp to be localized.

The invention is not limited to the shown and disclosed embodiments, but other elements, improvements and variations are also in the scope of the invention. It is clear for those skilled in the art, that the method for qualifying electric circuits and localizing a weak or bad contacting joint or contact of an electric circuit can be used for testing or qualifying any electric circuit made of different metal materials such as electric circuits in automobiles or machines. The use of these methods is not limited to detecting a weak or bad contacting joint, but adaptable to detecting the absence of parts in a circuit. For example, a closed electric circuit of an electric generator without a carbon brush must be differed from the similar circuit with carbon brush in place.

The invention claimed is:

1. A post-manufacture method for qualifying a completed electric circuit having at least one electric joint or contact comprising the steps of:
   providing a reference function of thermoelectric voltage versus time of a faultless electric circuit subsequent to manufacture of the completed circuit,
   heating the electric circuit by at least one measuring electric impulse,
   acquiring the thermoelectric-voltage-versus-time data of the electric circuit,
   comparing the acquired thermoelectric-voltage-versus-time data to the reference function,
   qualifying the electric circuit based on the differences between the acquired data and the reference function.

2. The method of claim 1 in which the reference function is provided by modeling the behavior of the faultless electric circuit during its heating by the measuring electric impulses and its subsequent cooling.

3. The method of claim 1 in which the reference function is provided by measurement of the faultless electric circuit during heating by the measuring electric impulses and its subsequent cooling.

4. The method of claim 1 in which the measuring electric impulses are obtained from an impulse generator and the electric circuit is disconnected from the impulse generator subsequently to the falling edge of the electric impulses.

5. The method of claim 1 in which the data acquisition has a sampling frequency higher than 1 kHz.

6. The method of claim 1 in which the data acquisition has a voltage range of 0.5-5 mV.

7. The method of claim 1 in which two or more measuring electric impulses are applied to the electric circuit.

8. The method of claim 7 in which the measuring electric impulses have different lengths.

9. The method of claim 1 in which the qualification of the electric circuit is based on the differences in shape of graphs plotted of the acquired thermoelectric-voltage-versus-time data and the reference function.

10. A method of qualifying an electric circuit having at least one joint or contact comprising the steps of:
    providing a reference function of thermoelectric voltage versus time of a faultless electric circuit,
    heating the electric circuit by At least one measuring electric impulse that is between 1-14 V and the lengths of the measuring electric impulses are between 5-30 ms,
    acquiring the thermoelectric-voltage-versus-time data of the electric circuit,
    comparing the acquired thermoelectric-voltage-versus-time data to the reference function,
    qualifying the electric circuit based on the differences between the acquired data and the reference function.

11. A post-manufacture method for localizing a weak or bad contacting joint or contact of a completed electric circuit, the method comprising the steps of:
    providing reference functions of thermoelectric voltage versus time of different possible locations of the weak or bad contacting joint or contact of the electric circuit subsequent to manufacture of the completed circuit,
    heating the electric circuit by at least one measuring electric impulse,
    acquiring thermoelectric-voltage-versus-time data of the electric circuit,
    comparing the acquired thermoelectric-voltage-versus-time data to the reference functions,
    localizing the weak or bad contacting joint or contact of the electric circuit in accordance with the similarities between the acquired data and reference functions.

12. The method of claim 11 in which the reference functions are provided by measurement of defective electric circuits with different locations of the weak or bad contacting joint or contact.

13. The method of claim 11 in which the measuring electric impulses are obtained from an impulse generator and the electric circuit is disconnected from the impulse generator subsequently to the falling edge of the electric impulses.

14. The method of claim 11 in which the data acquisition has a sampling frequency higher than 1 kHz.

15. The method of claim 11 in which the data acquisition has a voltage range of 05-5 mV.

16. The method of claim 11 in which two or more measuring electric impulses are applied to the electric circuit.

17. The method of claim 16 in which the measuring electric impulses have different lengths.

18. The method of claim 11 in which the localization of the weak or bad contacting joint or contact of the electric circuit is based on the similarities in shape of graphs plotted of the acquired thermoelectric-voltage-versus-time data and the reference functions.

19. A method of localizing a weak or bad contacting joint or contact of an electrical circuit, the method comprising the steps of:
    providing reference functions of thermoelectric voltage versus time of different possible locations of the weak or bad contacting joint or contact of the electric circuit, heating the electric circuit by at least one measuring electric impulse that is between 1-14 V and the length of the at least one measuring electric impulse is between 5-30 ms, acquiring the thermoelectric-voltage-versus-time date of the electric circuit, comparing the acquired thermoelectric-voltage-versus-time data to the reference functions, localizing the weak or bad contacting joint or contact of the electric circuit in accordance with the similarities between the acquired data and reference functions.

* * * * *